US 6,524,601 B1

(12) United States Patent
Shapiro et al.

(10) Patent No.: US 6,524,601 B1
(45) Date of Patent: Feb. 25, 2003

(54) FORMULATED ARTHROPOD CADAVERS FOR PEST SUPPRESSION (75) Inventors: David I. Shapiro, Macon, GA (US); Robert Behle, Morton, IL (US); Michael R. McGuire, Bakersfield, CA (US); Edwin E. Lewis, Blacksburg, VA (US)

(73) Assignees: The United States of America as represented by the Secretary of Agriculture, Washington, DC (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/875,972

(22) Filed: Jun. 8, 2001

(51) Int. Cl.$^7$ .................. A01N 25/00; A01N 25/24; A01N 25/34; A01N 25/26; A01N 9/50

(52) U.S. Cl. .................. 424/405; 424/407; 424/408; 424/409; 424/410; 424/418; 424/499

(58) Field of Search .................. 424/75, 405, 407, 424/408, 409, 410, 418, 499

(56) References Cited

U.S. PATENT DOCUMENTS

| | | | |
|---|---|---|---|
| 4,859,377 A | | 8/1989 | Shasha et al. |
| 5,172,514 A | | 12/1992 | Weber et al. |
| 5,358,863 A | * | 10/1994 | Quimby, Jr. et al. ........ 424/405 |
| 5,965,149 A | * | 10/1999 | Silver ......................... 424/405 |
| 5,997,945 A | * | 12/1999 | Shasha et al. ............... 424/405 |
| 6,057,145 A | | 5/2000 | Ishibashi |
| 6,184,434 B1 | | 2/2001 | Raulston et al. |

OTHER PUBLICATIONS

Creighton et al., Heterorhabditis sp. (Nematoda:Heterorhabditidae): A Nematode Parasite Isolated from the Banded Cucumber Beetle *Diabrotica balteata*, J. Nematology, vo. 17, (2), pp. 150–153, 1985.*

Jansson et al., "Field Efficacy and Persistence of Entomopathogenic Nematodes (Rhabditida: Steinemematidae, Heterorhabditidae) for Control of Sweetpotato Weevil (Coleoptera:Apionidae) in Southern Florida", J. Econ. Entomol., vol. 86, (4), pp. 1055–1063, 1993.*

Creighton, C.S. et al., Heterorhabditis sp. (Nematoda: Hetererhabditidae) : A Nematode Parasite Isolated from the Banded Cucumber Beetle *Diabrotica balteata*, J. of Nematology, vol. 17, (2), pp. 150–15, 1985.

Jansson, R. et al., "Field Efficacy and Persisitence of Entomopathogenic Nematodes (Rhabditida: Steinernematidae, Heterorhabditidae) for Control of Sweetpotato Weevil (Coleoptera: Apionidae) in Southern Florida", J. Econ. Entomol., vol. 86, (4), pp. 1055–1063, 1993.

Shapiro, D. et al., "Comparison of Entomopathogenic Nematode Dispersal from Infected Hosts Versus Aqueous Suspension", Environ. Entomol., vol. 25, (6), pp. 1455–1461, 1996.

Shapiro, D. et al., "Comparison of Entomopathogenic Nematode Infectivity from Infected Hosts Versus Aqueous Suspension", Environ. Entomol., vol. 28, (5), pp. 907–911, 1999.

(List continued on next page.)

Primary Examiner—Thurman K. Page
Assistant Examiner—Blessing Fubara
(74) Attorney, Agent, or Firm—M. Howard Silverstein; John D. Fado; Gail E. Poulos (57) ABSTRACT

Pesticidal and/or antimicrobial biological agent-infected arthropod cadavers are formulated by applying a coating agent once on the surface of the cadaver which either (a) prevents the cadavers from sticking together and/or rupturing or (b) acts as an adhesive for a powder or granule applied to the cadaver to prevent sticking and rupturing. The formulated cadavers maintain or improve infectivity, reproducibility, and survivability. The formulated cadavers can be partially desiccated to improve on shelf-life.

41 Claims, 3 Drawing Sheets

OTHER PUBLICATIONS

McGuire, M. et al., "Formulation of Microbial Pesticides", *H.B. Scher (ed) Controlled–release Delivery Systems for Pesticides*, pp. 173–193, 1999.

Shapiro, D., et al., "Comparison of Entomopathogenic Nematode Infectivity from Infected Hosts Versus Aqueous Suspension", *Environ. Entomol.*, vol. 28, (5), pp. 907–911, 1999.

Koehler, P., et al., "Susceptibility of Cockroaches (Dictyoptera: Blattellidae, Blattidae) to Infection by *Steinernema carpocapsae*", *J. Econ. Entomol.* vol. 85, (4), pp. 1184–1187, 1992.

Li, J., et al., "Bacterial Symbionts of Entomopathogenic Nematodes– Useful Sources of Bioactive Materials", *Canadian Chemical News*, vol. 49, Issue #6, pp. 15–16, 1997.

Gaugler, R., et al., "Entomopathogenic Nematodes in Biological Control", CRC Press, pp. 153–172, Boca Raton, Florida, 1990.

Gaugler, R., et al.,"Entomopathogenic Nematodes in Biological Control", CRC Press, pp. 173–191, Boca Raton, FL, 1990.

Gaugler, R., et al., "Entomopathogenic Nematodes in Biological Control", CRC Press, pp. 23–61, Boca Raton, FL, 1990.

Caroli, L., et al., "Entomopathogenic Nematode Infectivity Assay: Comparison of Penetration Rate into Different Hosts", *Biocontrol Science and Technology*, vol. 6, pp. 227–233, 1996.

Georgis, R., et al., "Formulation of Entomopathogenic Nematodes", *American Chemical Society*, Chapter 13, pp. 197–205, 1995.

Kaya, H. et al., "Entomopathogenic Nematodes", *Annu. Rev. Entomol.*, vol. 38, pp. 181–206, 1993.

Mauleon, H., et al., "Utilisation D'Enzymes Digestives Pour L'Etude Du Parasitisme Des Steinernema Et Des Heterorhabditis Envers Les Larves D'Insectes", *Fundam. Appl. Nematol.*, vol. 16, (2), pp. 185–191, 1993.

Womersley, C., "Factors affecting Physiological Fitness and Modes of Survival Employed by Dauer Juveniles and their Relationship to Pathogenicity", *Nematodes and the Biological Control fo Pests*, Chapter 10, pp. 79–88.

Duncan, L.W., et al., "Entomopathogenic Nematodes as a Component of Citrus Root Weevil Ipm", *Optimal Use of Insecticidal Nematodes in Pest Management*, Proceedings of Workshop Aug. 28–30, pp. 69–78, New Brunswick, New Jersey, 1999.

Woodring, J., et al., *Steinernematid and Heterorhabditid Nematodes: A Handbook of Biology and Techniques*, pp. 1–29, Arkansas Agricultural Experiment Station, Fayetteville, Arkansas, Aug. 1988.

Koppenhofer, A., "Nematodes", *Field Manual of Techniques in Invertebrate Pathology*, Chapter 4–5, pp. 283–301, 2000.

Glazer, I., et al., "Activity and Persistence of Entomoparasitic Nematodes Tested Against *Heliothis armigera* (Lepidoptera: Noctuidae)", *Entomological Society of America*, vol. 90, pp. 1795–1800, 1990.

Grewal, P., et al., "Entomopathogenic Nematodes", *Methods in Biotechnology*, vol. 5, pp. 271–299, 1998.

* cited by examiner

FORMULATED ARTHROPOD CADAVERS FOR PEST SUPPRESSION

BACKGROUND OF THE INVENTION

1. Field of the Invention

This invention generally relates to compositions for preparing formulated arthropod cadavers containing biological organisms having pesticidal and/or antimicrobial activity, compositions containing formulated arthropod cadavers, and a method for preparing and using formulated arthropod cadavers.

2. Description of the Related Art

Control of pest and/or microbial infestations and the direct loss caused by infestations are costly. Myriad approaches have been pursued to control pests. It is well known to encapsulate fungi, bacteria, and nematodes in alginate or starch matrices. Wheat gluten also has been employed for encapsulation. Ordinarily, the encapsulated product is in the form of granules (i.e., pellets or particulates) that are dispersed or sprayed directly upon or in the locus of an area infested with weeds, insects, diseases, and nematodes that are harmful to plants and agricultural crops. The purpose of the biocontrol agent is to control (e.g., reduce the population or growth, or possibly eliminate) the target pest. One of the problems associated with such encapsulated biocontrol agents is that the granules tend to dry out too quickly, which is harmful to the agent since moisture is necessary for their survival.

Entomopathogenic nematodes are just one example of a biocontrol agent which can be formulated into a carrier to control pests. Entomopathogenic nematodes in the genera Steinernema and Heterorhabditis are obligate parasites of insects (Kaya and Gaugler, Entomopathogenic nematodes, Annu. Rev. Entomol., Volume 38, 181–206, 1993). Entomopathogenic nematodes are biological control agents that generally infect their host by entering natural openings in the host. Heterorhabditids also have the ability to enter certain hosts through the cuticle using a tooth. After entering a host, symbiotic bacteria are released, the nematodes molt and reproduce, and after 1–3 generations, dauer stage juveniles emerge. The dauer juvenile stage is the only stage that is capable of surviving and infecting new hosts in the natural environment. Infective juveniles enter the host and release symbiotic bacteria which aid in (a) killing the host, (b) providing nutrients to the nematodes, and (c) releasing antibiotics, which prevent invasion by other microbes; the bacteria, however cannot survive outside of the host in a natural environment (e.g. soil) without the nematode (Poinar, Biology and taxonomy of Steinernematidae and Heterorhabditidae, In: Entomopathogenic Nematodes in Biological Control, R. Gaugler and H. K. Kaya, Eds., 23–62, 1990, CRC Press, Boca Raton, Fla.). The number of nematodes produced per insect varies among nematode species, and within species in different hosts. *Heterorhabditis bacteriophora* Poinar, for example, can produce over 500,000 infective juveniles per *Galleria mellonella* (L.) larva.

Entomopathogenic nematodes are important biological control agents for a variety of economically important pests in agricultural and urban environments (Grewal and Georgis, Entomopathogenic nematodes, IN: "Methods in Biotechnology", Volume 5, Biopesticides: Use and Delivery, F. R. Hall and J. J. Menn, Eds., 271–299, 1998, Totowa, N. J., Humana Press, Inc.; Kaya and Gaugler, 1993, supra). The nematodes can be mass-produced using in vivo and in vitro methods (Friedman, Commercial production and development, In: "Entomopathogenic Nematodes in Biological Control, R. Gaugler and H. K. Kaya, Eds., 153–172, 1990 Boca Raton, Fla., CRC Press). Entomopathogenic nematodes are commercially applied as infective juveniles in aqueous suspensions using various irrigation systems, sprayers, or injection techniques (Georgis, Formulation and application technology, IN: "Entomopathogenic Nematodes in Biological Control, supra, 173–194, 1990; Koppenhofer, Nematodes, IN: "Field Manual of Techniques in Invertebrate Pathology", L. A. Lacey and H. K. Kaya, Eds., 283–301, 2000, Kluwer Academic Publishers, Dordrecht).

Research indicates that entomopathogenic nematodes may also be applied in infected cadavers [(Creighton and Fassuliotis, Heterorhabditis sp. (Nematoda: Heterorhabditidae): A nematode parasite isolated from the banded cucumber beetle *Diabrotica balteata*, J. Nematology, Volume 17, 150–153, 1985; Jansson et al., Field efficacy and persistence of entomopathogenic nematodes (Rhabditida: Steinernematidae, Heterorhabditidae) for control of sweet potato weevil (Coleoptera: Apionidae) in Southern Florida, J. Econ. Entomology, Volume 86, 1055–1063, 1993)]. In this approach, nematode-infected cadavers are disseminated and pest suppression is subsequently achieved by the progeny infective juveniles that exit the cadavers. Laboratory studies indicate that nematode application in infected-hosts may be superior to application in aqueous suspension (Shapiro and Glazer, Comparison of entomopathogenic nematode dispersal from infected hosts versus aqueous suspension, Environ. Entomol., Volume 25, 1455–1461, 1996; Shapiro and Lewis, Comparison of entomopathogenic nematode infectivity from infected hosts versus aqueous suspension, Environ. Entomol., Volume 28, 907–911, 1999). However, commercialization of nematode-infected cadavers has been prevented due to problems in storage and application (Koppenhofer, 2000, supra). Nematode-infected hosts stick together or rupture during transport and/or application, which results in reduced efficacy. Formulation of nematode-infected cadavers can overcome these problems by providing shelf-life, stability of product from transport to application, and ease of handling (Georgis et al., Formulation of entomopathogenic nematodes, In:"Biorational Pest Control Agents: Formulation and Delivery, F. R. Hall and J. W. Barry, Eds., 197–205, 1995, Washington, D.C.: American Chemical Society). Entomopathogenic nematodes have been formulated for commercial application in various carriers including clay, activated charcoal, sponge, vermiculite, peat, alginate gels, and water dispersible granules (Georgis, 1990, supra; Georgis et al., 1995, supra). Shelf-life, in most formulations, is enhanced by reducing nematode metabolism through partial desiccation, and, or , storage at low temperatures such as, for example, about 4–15° C. (Georgis et al., 1995, supra). Desiccation is a common method used during entomopathogenic nematode formulation to increase shelf-life by decreasing nematode metabolism. The anhydrobiotic potential of entomopathogenic nematodes, however is limited. If the rate of desiccation is inappropriate, high nematode mortality occurs. For example, 100% mortality was reported in *S. carpocapsae* (Weiser) after three days exposure to 60% relative humidity or one day exposure to 0 or 40% relative humidity (Womersley, Factors affecting physiological fitness and modes of survival employed by dauer juveniles and their relationship to pathogenicity; IN: "Nematodes for the Biological Control fo Insects"; R. A. Bedding et al., eds; 79–88, CSIRO Press, East Melbourne, Australis; 1993). *Heterorhabditis bacteriophora* has been found to be less desiccation tolerant than *S. carpocapsae* (Glazer and Navon, J. Econ. Entomology, Volume 83, 1795–1800, 1990). Koppenhofer (2000, supra) reported that entomopathogenic nematodes can survive dry conditions for extended periods if they remain inside a host cadaver.

Various formulations for entomopathogenic organisms are known, however there remains a need in the art for formulations which prolong shelf-life of formulated entomopathogens while at least maintaining infectivity and reproduction levels for effective biological control. The present invention, as described below, is different from related art formulations.

SUMMARY OF THE INVENTION

It is therefore an object of the present invention to provide a formulated arthropod cadaver containing a pesticidal and/or antimicrobial biological organism as a biocontrol agent in which at least viability and/or reproductive capacity of the biological organism in the formulated arthropod cadavers is improved over that of non-formulated arthropod cadavers.

Another object of the present invention to provide a formulated arthropod cadaver containing a pesticidal and/or antimicrobial biological organism as a biocontrol agent in which at least infectivity of the biological organism in the formulated arthropod cadavers is equal or greater than that of a non-formulated biocontrol agent-containing arthropod cadaver.

A still further object of the present invention is to provide a formulated arthropod cadaver containing a pesticidal and/or antimicrobial biological organism as a biocontrol agent in which at least storability of the biological agent in the formulated arthropod cadavers is improved over that of a non-formulated biocontrol agent-infected cadaver.

Another object of the present invention is to provide a method for formulating pesticidal and/or antimicrobial biological organisms in arthropod cadavers as a biological control agent in which viability and/or reproductive capacity is improved over that of non-formulated arthropod cadavers containing pesticidal and/or antimicrobial biological organisms.

A further object of the present invention is to provide a method for formulating pesticidal and/or antimicrobial biological organism-containing arthropod cadavers as a biocontrol agent in which infectivity of the biological organism is equal to or greater than that of non-formulated biological organism-containing arthropod cadavers.

A still further object of the present invention is to provide a method for formulating pesticidal and/or antimicrobial biological organism-containing arthropod cadavers as a biocontrol agent in which storability is improved over that of non-formulated cadavers.

A further object of the present invention is to provide a biocontrol agent that includes formulated pesticidal and/or antimicrobial biological organism-containing arthropod cadavers.

Further objects and advantages of the invention will become apparent from the following description.

DETAILED DESCRIPTION OF THE INVENTION

The present invention is useful for providing entomopathogenic biological organisms for pesticidal and/or antimicrobial control of pests or disease in both agricultural, commercial, and urban environments.

For purposes of the present invention entomopathogenic biological organisms for pesticidal and/or antimicrobial control of pests; include without limitation bacteria, such as for example, *Bacillus thuringiensis*; fungi, such as for example, *Beauveria bassiana*; yeasts, viruses, such as for example, nucleopolyhedrovirus; microsporidians, protozoa, and other lower organisms which are pathogenic toward target pests. Of course, any component or byproduct of the organism or stage of its life cycle which is infective to the host is considered to be within the scope of the invention. The term pesticidal and/or antimicrobial means that the biological organism is either pesticidal or antimicrobial, and includes a biological organism which has both pesticidal and antimicrobial activity, such as for example, an entomopathogenic nematode.

The present invention provides a composition and process for formulating pesticidal and/or antimicrobial biological organism-infected cadavers. In one embodiment of the present invention, the process for formulating pesticidal and/or antimicrobial biological organism-infected arthropod cadavers includes the steps of:

(a) admixing an effective amount of a coating compound, such as for example, a starch, carbohydrate, synthetic polymer, natural adhesive, oil, lipid, protein, and mixtures thereof with a liquid to form an aqueous or non-aqueous solution or suspension to form a first coating agent which (a) at least reduces or prevents the cadavers from sticking to each other and/or rupturing after the first coating agent has dried on the cadaver, or (b) facilitates the adherence of a second coating agent powder or granule;

(b) optionally including a fungicide in the first coating agent in an amount effective to prevent fungus contamination of the formulated arthropod cadavers;

(c) applying to a pesticidal and/or antimicrobial biological organism-infected arthropod cadaver a first coating agent until it is coated with said coating agent to form a formulated infected arthropod cadaver;

(d) optionally applying a second coating agent which is an adsorbent powder or granule for a time until adhesion of the powder or granule is maximized to form a formulated infected arthropod cadaver; and (e) optionally, to improve shelf-life, desiccating the formulated infected arthropod cadavers.

For purposes of the present invention, the term arthropod encompasses insects, arachnids, and crustaceans.

The first coating agent coats the surface of the cadaver and serves (a) to form a non-stick surface on the cadaver after it has dried or (b) as an adhesive for a second coating agent powder or granule. For purposes of the present invention, the first coating agent is an aqueous or nonaqueous solution or suspension of a coating compound in amounts effective to cause (a) the surface of the infected arthropod cadaver to be non-sticky to prevent cadavers from sticking together and/or rupturing or (b) the second coating agent to adhere to the infected arthropod cadavers. Any coating compound is useful in the invention if it accomplishes (a) and/or (b) above and does not affect the reproducibility and/or infectivity of the pesticidal and/or antimicrobial agent.

The second coating agent, adsorbent powders or granules, prevents nematode-infected insect cadavers from sticking together and rupturing. For purposes of the present invention, the second coating agent includes powders or granules such as hydrated silica, fumed silica, kaolin, silicate and other clays, corn bran, oat bran, wheat bran and other brans of grain, diatomaceous earth, zeolite, titanium dioxide and absorbent starch, cold-swelling starch, lignin, and mixtures thereof. It is used in amounts effective to at least reduce sticking and/or rupturing of the formulated cadavers. Any powder or granule is useful in the invention if it at least reduces sticking and/or rupture of the formulated cadavers and does not affect the reproducibility and/or infectivity of the pesticidal and/or antimicrobial agent.

Antifungal agents such as, for example, methyl paraben and sorbic acid, can optionally be included in amounts effective to at least reduce fungal contamination of the biological organism-infected insect cadavers. Any antifungal agent which does not reduce reproduction or infectivity of the biological organism is useful in the present invention. The antifungal agent is added to the first coating agent.

Optionally, at least one plasticizer can be added to the first coating agent. Examples of such plasticizers include at least one member selected from the group consisting of polyethylene glycol, glycerol, propylene glycol, carnauba wax, candelilla wax, stearic acid, oleic acid, sorbitol, soybean oil, beeswax, mannitol, and mixtures thereof.

Desiccation of formulated biological organism-infected arthropod cadavers can be accomplished using any known method for desiccation, such as for example, holding at about 0% relative humidity for about one week using anhydrous calcium sulfate.

Other additives and adjuncts may be formulated into the subject compositions. Examples of these include UV protectants, preservatives, and inert fillers.

In a second embodiment of the present invention, the process for formulating pesticidal and/or antimicrobial biological organism-infected arthropod cadavers includes the steps of:

(a) applying a second coating agent powder or granule to a pesticidal and/or antimicrobial biological organism-infected arthropod cadaver until the powder or granule has adhere to said cadaver in an amount effective to at least reduce sticking together of the formulated cadavers and/or reduce rupture of the formulated cadavers;

(b) optionally including a fungicide in the second coating agent powder or granule in an amount effective to prevent fungus contamination of the formulated arthropod cadavers; and (c) optionally desiccating the formulated infected arthropod cadavers to improve shelf-life.

For purposes of the present invention, in the second embodiment, the second coating agent powder or granule can be applied directly to the infected cadaver or to an infected cadaver that has first been wetted with water. Furthermore, the second coating agent powder or granule can be mixed with a starch prior to application to facilitate sticking of the powder or granule to the dry or wetted cadaver.

The target pests for control by means of the subject formulated biological organism-infected insect cadavers include arthropods or other non-vertebrate pests in urban, commercial, or agricultural environments (Grewal and Georgis, 1998, supra; Koehler et al., Susceptibility of cockroaches (Dictyoptera: Blatellidae, Blattidae) to infection by *Steinernema carpocapsae*, J. Econ. Entomol., Volume 35, 1184–1187, 1992; Weber et al., U.S. Pat. No. 5,172,514, 1992) or to suppress microbial agents of agricultural or medical importance (Li and Webster, Bacterial symbionts of entomopathogenic nematodes-useful sources of bioactive materials, Canadian Chemical News, Volume 49, 15–16, 1997).

To illustrate the above described invention nematode-infected insect cadavers are used that have been coated with starch or protein and rolled in a second coating agent powder or granule. An example of such formulations is a nematode-infected insect cadaver containing infective juveniles using *H. bacteriophora* and *Galleria mellonella* (L.) as a model nematode and host, respectively. Any entomopathogenic nematode infective juveniles and host cadaver may be used. *Heterorhabditis bacteriophora* is a versatile nematode that has been marketed against a wide variety of economically important pests such as the black vine weevil, Diaprepes root weevil, and white grubs (Duncan et al., Entomopathogenic nematodes as a component of citrus root weevil IPM, In: "Optimal use of Insecticidal Nematodes in Pest Management", S. Polavarapu, Ed., 69–78, 1999, New Brunswick, N.J.:Rutgers University; Grewal and Georgis, Entomopathogenic nematodes, In:"Methods in Biotechnology, Volume 5, Biopesticides: Use and Delivery, F. R. Hall and J. J. Menn, Eds., 271–299, 1998, Totowa, N.J.: Humana Press). *Galleria mellonella* is the most commonly used insect for in vivo mass production of entomopathogenic nematodes (Grewal and Georgis, 1998, supra) because it produces high nematode yields, is widely available commercially, and is very susceptible to infection (Woodring and Kaya, Steinernematid and Heterorhabditid Nematodes: A handbook of Biology and Techniques, Southern California Cooperative Series Bulletin 331, Arkansas Agricultural Experiment Station, Fayetteville, Ark., 1998).

The starch can be any granular starch. Starch is a low-cost and abundant natural carbohydrate polymer composed of amylose and amylopectin. Amylose is primarily linear, containing anywhere from 200 to 2,000 anhydroglucose units linked together by D(1,4) glycosidic bonds. Amylopectin is a branched polymer, also connected by D(1,4) glycosidic linkages but with periodic branch points created by D(1,6) glucosidic bonds. Amylopectin is typically much larger than amylose, with molecular weights in the millions. In native form, most starches contain about 18% to about 28% amylose with the remainder amylopectin. Corn and wheat starches contain approximately 28% amylose, while potato, tapioca and rice varieties are closer to about 20%.

Cold-swelling starches are starches that are instantized without gelatinization to physically disrupt internal granular structure. These starches provide excellent dispersion, sheen, and texture. An example of these starches are Mira-Sperse starches (A. E. Staley Manufacturing Company).

Protein for purposes of the present invention includes any plant protein such as for example, glutens or zeins from any source of plant such as wheat, corn, oats, rice, soybean, and mixtures thereof or animal proteins such as casein, whey, fish myofibular protein, etc.

The following examples are intended only to further illustrate the invention and are not intended to limit the scope of the invention which is defined by the claims. *Heterorhabditis bacteriophora* Poinar and *Galleria mellonella* are used as a model for the present invention.

EXAMPLE 1

*Heterorhabditis bacteriophora* (Hb strain) were cultured in last instar *Galleria mellonella* larvae according to procedures described in Woodring and Kaya (Steinernematid and Heterorhabditid Nematodes: A handbook of Biology and Techniques, Southern Cooperative Series Bulletin 331, Arkansas Agricultural Experiment Station, Fayetteville, Ark., 1988) Infected cadavers were produced by exposing each insect to approximately 50 infective juveniles in 50 mm petri dishes lined with filter paper (Whatman No. 1, for example). Nematode infection, development, and reproduction were carried out at approximately 100% relative humidity and about 25° C.

Four day-old and 8 day-old nematode-infected cadavers were dunked in an aqueous first coating agent for at least about three seconds and then rolled in a second coating agent which is an adsorbent powder or granule until adhesion of the powder or granule was maximized. Nineteen combinations were tested and are listed below in Table 1. Nine of the formulations failed to adhere to both 4 and 8 day-old cadavers. The remaining formulated cadavers were placed on modified White Traps (Woodring and Kaya, 1988, supra). Progeny infective juveniles were collected and, after emergence ceased (about 25 days) the number produced per cadaver was determined through dilution counts (Woodring and Kaya, 1988, supra). There were five replicates (cadavers) per treatment including a non-formulated control. Four of the ten formulations in the first reproduction test did not produce any nematodes and were not investigated further (Table 1 below). The remaining six formulations were tested again twice (two identical trials) using the same experimental procedures as described above. In the first test with the ten formulations, opportunistic fungal growth was observed on a number of formulated cadavers, which may have inhibited nematode development. Therefore, in the second and third trials (with six formulations) the effects of incorporating two antifungal agents was determined. These two agents were Methyl paraben and sorbic acid.

Figure 1:
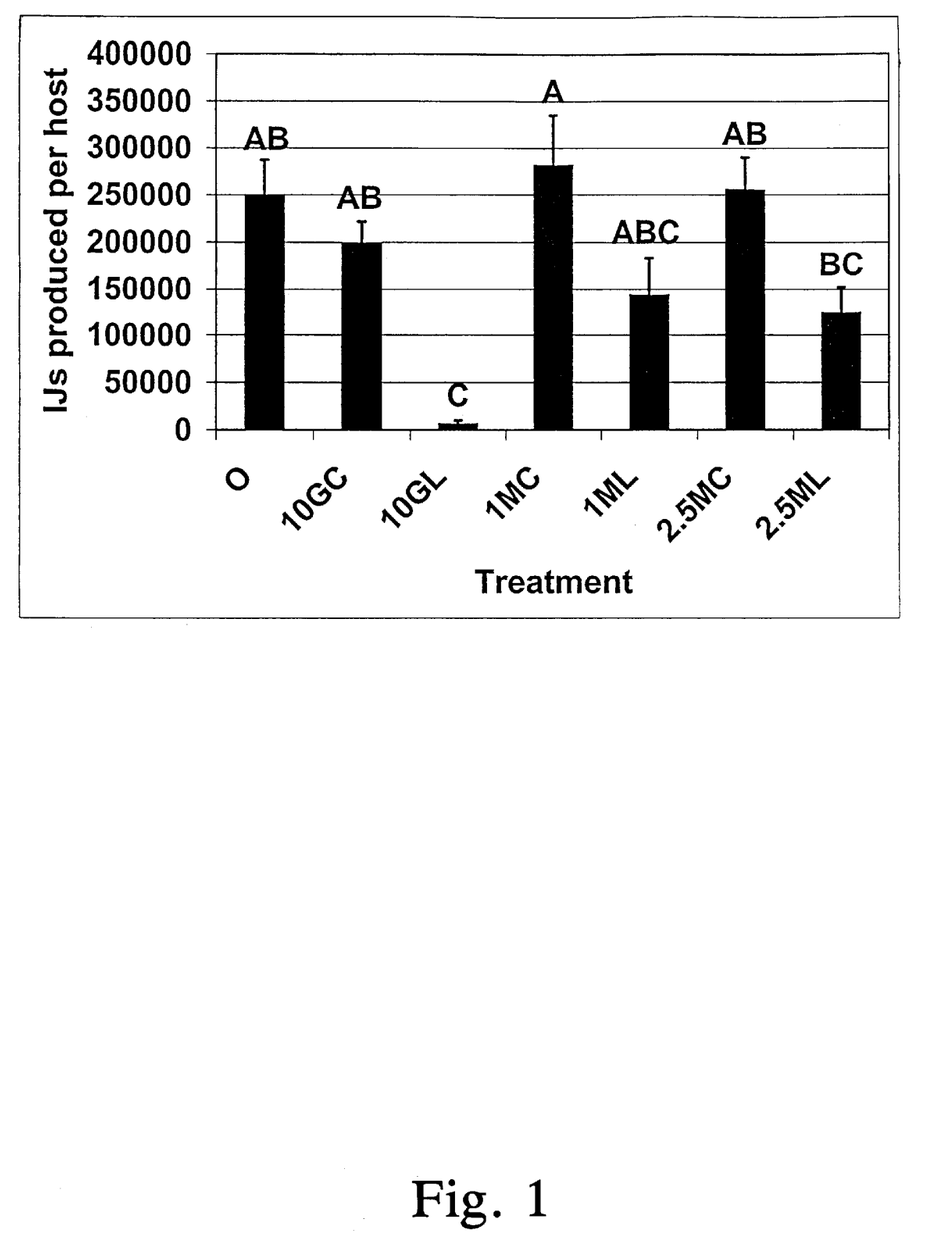
FIG. 1 is a graph showing numbers of *Heterorhabditis bacteriophora* infective juveniles (IJs) produced in *Galleria mellonella* cadavers, which were formulated 4 days post infection. O=non-formulated control; C=clay; 10G=10% gluten; L=lignin; M=Mira-Sperse (1 or 2%). Different letters above bars indicate statistical differences (Tukey's test, =0.05).
Figure 2:
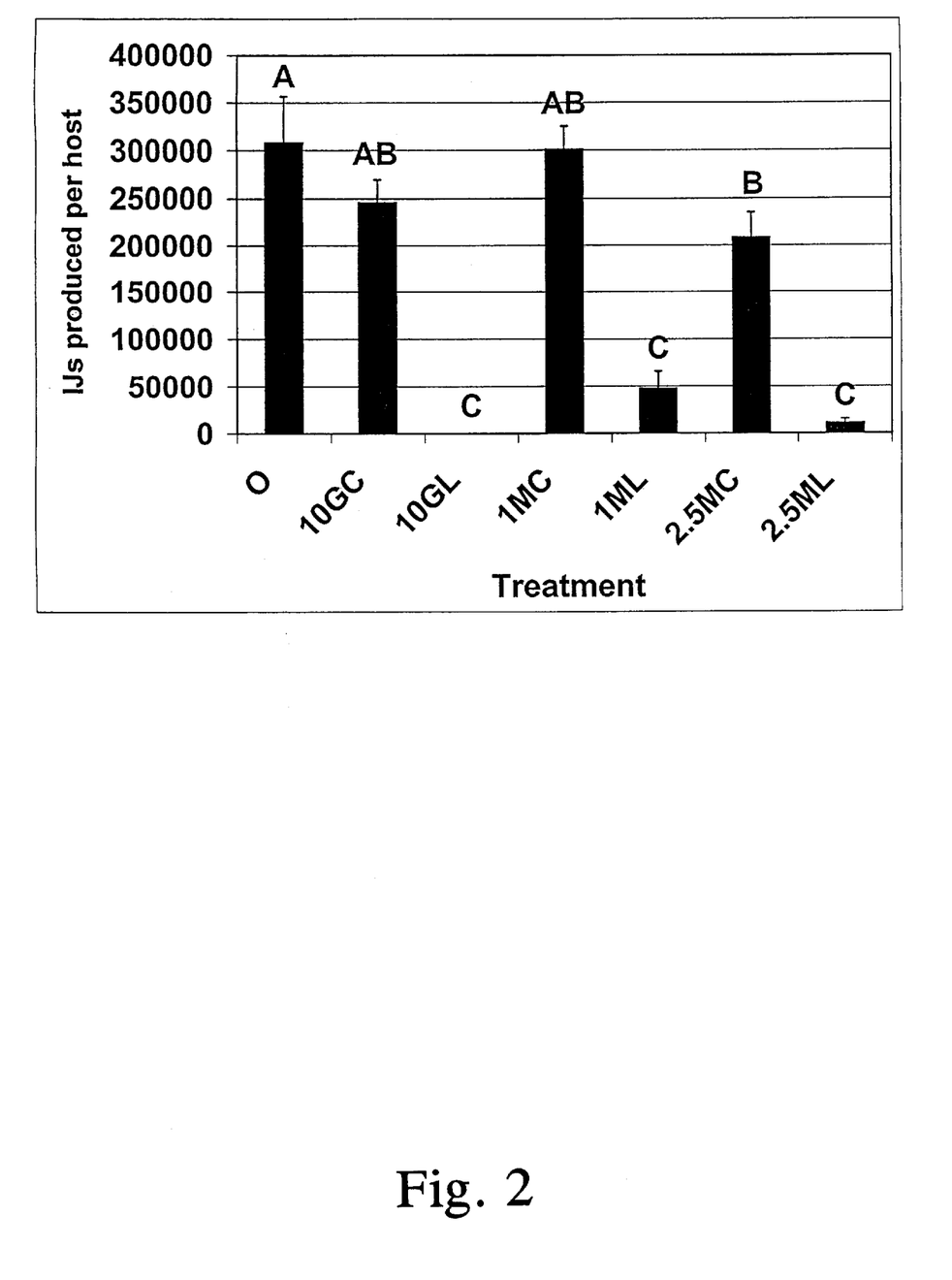
FIG. 2 is a graph showing numbers of *Heterorhabditis bacteriophora* infective juveniles (IJs) produced in *Galleria mellonella* cadavers which were formulated 8 days post infection. O=non-formulated control; C=clay; 10G=10% gluten; L=lignin; M=Mira-Sperse (1 or 2%). Different letters above bars indicate statistical differences (Tukey's test, =0.05).

Some of the formulations adhered to the cadavers and allowed nematode reproduction to proceed whereas others did not (See Table 1 below). Significant differences in the number of infective juveniles produced per cadaver were detected among the six formulations that exhibited reproduction and the non-formulated control (F=32.89; df=6,195; P=0.0001). No interactions were detected between treatment and trial or treatment and antifungal presence (P=0.19 and 0.17, respectively). A significant interaction was detected between time of formulation and treatment (F=4.47; df=6, 195; P=0.0003); thus data were not combined across these factors. The number of infective juveniles produced in formulated cadavers was similar to the number produced in non-formulated cadavers except in the 10% gluten/lignin formulation of 4 days post infection (FIG. 1) and in all formulations that included lignin 8 days post infection (FIG. 2). Four days post infection cadavers formulated with 1% Mira-Sperse (EXPROD C3-111, A. E. Staley Manufacturing Company)/clay produced more nematodes than cadavers formulated with 10%. gluten/lignin or 2.5% Mira-Sperse/ lignin. Eight days post infection cadavers formulated with lignin produced fewer nematodes than all other treatments.

Time of formulation affected reproduction in some treatments, whereas the presence or absence of antifungal agents did not. When averaged over all formulations, time of formulation did not significantly affect nematode reproduction (T=1.1; df=218; P=0.270). However, when treatments were analyzed individually, significant differences in reproduction were detected ((P>0.05) in 1% Mira-Sperse/lignin (4 days post infective>8 days post infective), and in the 2.5% Mira-Sperse/lignin (4 day post infective >8 day post infective); no other differences were detected between days. Percentages of cadavers exhibiting opportunistic fungal growth in formulations with and without antifungal agents were (mean±se) 3.3±3.3, and 16.7±8.0,respectively, these means were not significantly different (T=−1.53; df=10; P=0.156). The presence of antifungal agents did not significantly (P<0.05) affect nematode reproduction in any of the formulation treatments.

TABLE 1

Combinations of materials tested for formulating *Heterorhabditis bacteriophora*-infected *Galleria mellonella*.

| First Coating Agent[a] | Second Coating Agent[b] | Abbreviation | Result[c] |
|---|---|---|---|
| 2% Agar | titanium dioxide | 2 AT | pa |
| 20% Gluten | clay (calcium silicate) | 20 GC | a, nr |
| 20% Gluten | lignin | 20 GL | a, nr |
| 20% Gluten | titanium dioxide | 20 GT | pa |
| 10% Gluten | clay[b] | 10 GC | a, r |
| 10% Gluten | lignin | 10 GL | a, r |
| 1% Mira-Sperse[c] | clay | 1 MC | a, r |
| 1% Mira-Sperse | lignin | 1 ML | a, r |
| 2.5% Mira-Sperse | Mira-Sperse | 2.5 MM | pa |
| 2.5% Mira-Sperse | clay (calcium silicate) | 2.5 MC | a, r |
| 2.5% Mira-Sperse | lignin | 2.5 ML | a, r |
| 2.5% Mira-Sperse | titanium dioxide | 2.5 MT | pa |
| 5% Mira-Sperse | clay | 5 MC | a, nr |
| 5% Mira-Sperse | Mira-Sperse | 5 MM | pa |
| 5% Mira-Sperse | lignin | 5 ML | a, nr |
| 5% Mira-Sperse | titanium dioxide | 5 MT | pa |
| 7.5% wheat starch | clay | 7.5 WC | pa |
| 7.5% wheat starch | corn flour | 7.5 WF | pa |
| 7.5% wheat starch | lignin | 7.5 WL | pa |

[a]gluten, wheat gluten (Midwest Grain Products, Atchison, KS); Mira-Sperse, a starch (ARE Staley Manufacturing Company, Decatur, IL).
[b]clay, calcium silicate (Mirocel, Manville Products Corporation, Denver, Colorado); lignin (PC-1307, Westvaco, Charleston Heights, SC); titanium dioxide (TiONA RCL9 BG0050, Millennium Inorganic Chemicals, Hunt Valley, MD).
[c]a = formulation adhered to host surface, pa = poor adhesion, nr = no reproduction observed (no infective juveniles emerged from host), r = reproduction observed.

EXAMPLE 2

Infectivity is defined as the number of nematodes invading a host. In this example, infectivity was compared among nematodes emerging from formulated and non-formulated cadavers four days post infection. Cadavers were formulated with either 1% Mira-Sperse as the first coating agent and clay as the second coating agent or 2.5% Mira-Sperse as the first coating agent and clay as the second coating agent. The formulated and non-formulated cadavers were placed on White traps and progeny nematodes were collected. Ten *G. mellonella* larvae were then exposed to the progeny-50 infective juveniles in about 0.35 ml of water from each treatment on 50 mm petri dishes lined with filter paper (Whatman No. 1). About two days post infection, the number of infective juveniles that penetrated the 10 insects was determined using a pepsin digestion method (Mauleon et al, Funda, Appl. Nematol., Volume 16, 185–186, 1993; Caroli et al., Biocontr. Sci. Technol., Volume 6, 227–233, 1996). Briefly, insects were rinsed to remove nematodes remaining on the cuticle and cut open longitudinally. The larvae were then placed in about 4 ml of pepsin solution (8 grams pepsin, 23 g NaCl, in 1000 ml $H_2O$; pH 2 with HCl) for 2 hours shaking constantly at about 200 rpm. Nematodes that had infected the larvae were then counted under dissecting microscopes. Larvae that were not counted immediately were stored at approximately −20° C. for up to one week.

Infectivity was not different among nematodes emerging from formulated versus non-formulated cadavers (F=0.12; df=224; P=0.8843). The average percentages of nematodes invading were (mean±se) 8.3±2.2, 7.8±2.0, and 9.8±2.3 for the 1% Mira-Sperse as the first coating agent and clay as second coating agent, 2.5% Mira-Sperse as the first coating-agent and clay as second coating agent, and control, respectively.

EXAMPLE 3

The effects of partial desiccation on nematode reproduction was compared in three formulations and a non-formulated control. The three formulations were 1% Mira-Sperse as the first coating agent and clay as second coating agent; 2.5% Mira-Sperse as the first coating agent and clay as second coating agent; and 10% gluten as the first coating agent and clay as the second coating agent. Cadavers were produced and formulated 4 and 8 days post infection as described above in example 1. One half of the formulated and non-formulated cadavers were placed directly into White traps and held at approximately 100% relative humidity for determination of nematode reproduction. The other half of the cadavers were placed in 60 mm petri dishes lined with dry filter paper (Whatman No. 1). These petri dishes were placed in polypropylene desiccators (Nalgene, 250 mm i.d.) and held at approximately 0% relative humidity which was achieved using anhydrous calcium sulfate (Drierite, W. A. Hammond Drierite Co., Xenia, Ohio). After one week the desiccated cadavers were removed and placed on White traps for determination of reproduction as described above in Example 1. No antifungal agents were added to the first coating agent. There were five replicates per treatment (3 formulations plus a control×2 times of formulation× desiccated vs not desiccated) and the study was repeated once (i.e., two trials).

Figure 3:
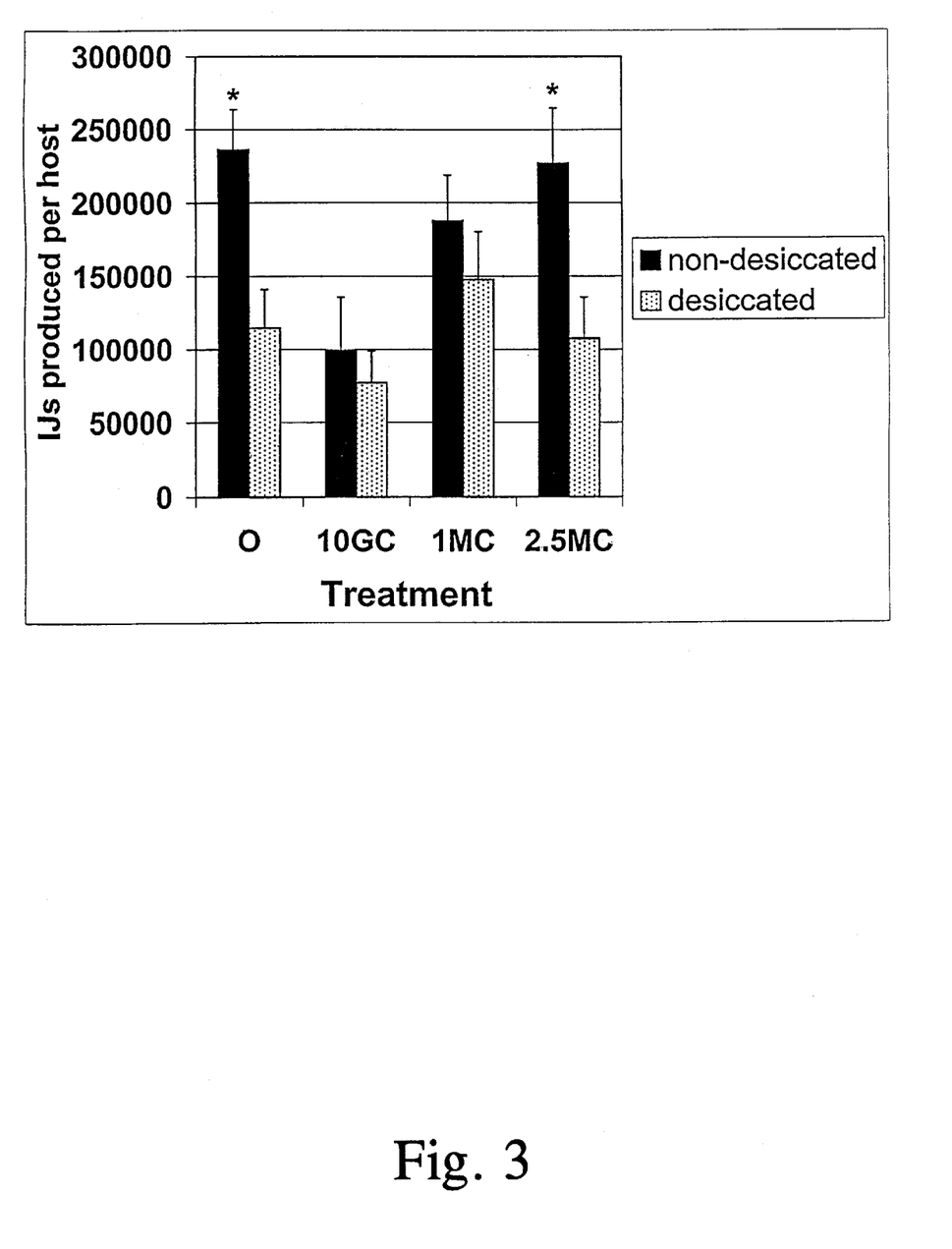
FIG. 3 is a graph showing numbers of *Heterorhabditis bacteriophora* infective juveniles (IJs) produced in desiccated and non-desiccated *Galleria mellonella* cadavers which were formulated 4 and 8 days post-infection. O=honformulated control; C=clay; 10G=10% gluten; L=lignin; M=Mira-Sperse (1 or 2%). Different letters above bars indicate statistical differences (Tukey's test, =0.05).

Effects of desiccation on formulated and non-formulated *H. bacteriophora*-infected cadavers varied among treatments. No interactions were detected between time of formulation and treatment, or trial and treatment; thus, the data were combined across factors. Relative to non-desiccated cadavers, reproduction in desiccated cadavers was reduced in non-formulated cadavers (T=−3.21; df=38; P=0.003) and cadavers formulated with 2.5% Mira-Sperse as the first coating agent and clay as the second coating agent (T=−2.538; df=38; P=0.015)(FIG. 3). Desiccation did not affect reproduction in cadavers formulated with about 1% Mira-Sperse as the first coating agent and clay as the second coating agent (T=−0.896; df=38; P=0.376) or 10% gluten as the first coating agent and clay as the second coating agent (T=−0.527; df=32; P=0.602) (FIG. 3). In non-desiccated cadavers, reproduction in formulated cadavers was not significantly different from non-formulated cadavers except for the about 10% gluten as the first coating agent and clay as the second coating agent combination in which case the formulation was detrimental to reproduction (F=3.94; df=7, 159; P=0.0006; TUKEY's Test P<0.05). In all treatments (including the non-formulated control), 4 day post infected cadavers produced more nematodes than 8 day post infected cadavers following desiccation (P<0.05). No nematode emergence occurred during desiccation; in all treatments emergence was delayed until cadavers were placed on White Traps.

EXAMPLE 4

The tendency to rupture or stick together was evaluated in formulated and non-formulated cadavers 2 and 9 days post infection. Two formulations-(a) 1% Mira-Sperse as the first coating agent and clay as the second coating agent (b) 2.5% Mira-Sperse as first coating agent and clay; were chosen for this example. Five cadavers of each formulation and 5 that were non-formulated were placed in 100 mm petri dishes. The petri dishes were taped together in random order shaken vigorously for about 10 seconds. The cadavers in each petri dish were then examined and the percentage ruptured and sticking together was recorded. There were five replicates of each treatment and time of formulation.

Formulated cadavers had less tendency to rupture and stick together than non-formulated cadavers both 2-days post infection (F=7.82; df=2,6; P=0.021, and F=10,000; df=2,6; P=0.0001 for rupture and sticking together, respectively) and 9 days post infection (F=10,000; df=2,6; P=0.0001 and F=38.62; df=2,6; P=0.0004 for rupture and sticking together, respectively). In 2-day-old non-formulated cadavers, 20±8.2% (mean±se) ruptured and 100% stuck together. In 9-day-old non-formulated cadavers, 80±8.2% ruptured and 80±11.6 stuck together. None of the formulated cadavers were observed to either rupture or stick together.

The foregoing detailed description is for the purpose of illustration. Such detail is solely for that purpose and those skilled in the art can make variations therein without departing from the spirit and scope of the invention.

What is claimed is:

1. A method for formulating pesticidal and/or antimicrobial biological organism-infected arthropod cadavers comprising:
   (a) admixing an effective amount of a coating compound in a liquid to form a first coating agent wherein said coating agent provides a surface on a biological organism-infected arthropod cadaver which at least reduces sticking and/or rupture of said cadavers; and
   (b) applying to biological organism-infected arthropod cadavers said first coating agent to form a formulated cadaver with a surface that at least reduces sticking and/or rupture of said cadavers.

2. The method of claim 1 wherein said first coating agent includes an antifungal agent.

3. The method of claim 1 further comprising desiccating said formulated arthropod cadavers.

4. The method of claim 1 wherein said coating compound is selected from the group consisting of starch, carbohydrate, synthetic polymer, adhesive, oil, lipid, protein, and mixtures thereof.

5. A method for formulating pesticidal and/or antimicrobial biological organism-infected arthropod cadavers comprising:
   (a) coating a biological organism-infected cadaver in a second coating agent to form a formulated biological organism-infected arthropod cadaver.

6. The method of claim 5 wherein said second coating agent includes an antifungal agent.

7. The method of claim 5 further comprising desiccating said formulated arthropod cadaver.

8. The method of claim 5 wherein said second coating agent is selected from the group consisting of silica, kaolin, silicate, clay, bran, diatomaceous earth, zeolite, titanium oxide, starch, lignin, and mixtures thereof.

9. A method for formulating pesticidal and/or antimicrobial biological organism-infected arthropod cadavers comprising:
   (a) admixing an effective amount of a coating compound in a liquid to form a first coating agent wherein said coating agent provides a surface on a biological organism-infected arthropod cadaver which at least reduces sticking and/or rupture of said cadavers;
   (b) applying to biological organism-infected arthropod cadavers said first coating agent to form a surface that facilitates the adherence of a second coating agent powder or granule; and
   (c) coating said cadaver with a first coating agent in a second coating agent to form a formulated biological organism-infected arthropod cadaver.

10. The method of claim 9 wherein said first coating agent includes an antifungal agent.

11. The method of claim 9 further comprising desiccating said formulated arthropod cadaver.

12. The method of claim 9 wherein said coating compound is selected from the group consisting of starch, carbohydrate, synthetic polymer, adhesive, oil, lipid, protein, and mixtures thereof.

13. The method of claim 9 wherein said second coating agent is selected from the group consisting of silica, kaolin, silicate, clay, bran, diatomaceous earth, zeolite, titanium oxide, starch, lignin, and mixtures thereof.

14. A method for formulating pesticidal and/or antimicrobial arthropod cadavers comprising:
   (a) admixing an effective amount of a starch with water to form a first coating agent wherein said agent provides a surface on a biological organism-infected arthropod cadaver which at least reduces sticking and rupture of said cadavers; and
   (b) applying said first coating agent to a biological organism-infected insect cadaver to form a surface on said cadaver that at least reduces sticking and rupture of said cadavers.

15. The method of claim 14 further comprising desiccating said formulated biological organism-infected arthropod cadaver.

16. The method of claim 14 wherein said starch is a cold-swelling starch.

17. A method for formulating pesticidal and/or antimicrobial biological organism-infected cadavers comprising:
   (a) admixing an effective amount of a starch with water to form a first coating agent wherein said agent provides an adhesive surface on said cadaver;
   (b) applying said first coating agent to a biological organism-infected arthropod cadaver to form an adhesive surface on said cadaver; and
   (c) coating said cadaver in a second coating agent selected from the group consisting of hydrated silica, fumed silica, kaolin, silicate, clay, bran, diatomaceous earth, zeolite, absorbent starch, lignin, and mixtures thereof; to form a formulated biological organism-infected arthropod cadaver.

18. The method of claim 17 further comprising desiccating said formulated biological organism-infected arthropod cadaver.

19. A method for formulating nematode-infected insect cadavers comprising:
   (a) admixing an effective amount of a starch with water to form a first coating agent wherein said agent provides an adhesive surface on said cadaver;
   (b) applying said first coating agent to a nematode-infected insect cadaver to form an adhesive surface on said cadaver; and
   (c) coating said cadaver in a second coating agent selected from the group consisting of silica, kaolin, silicate, clay, bran, diatomaceous earth, zeolite, absorbent starch, lignin, and mixtures thereof; to form a formulated nematode-infected insect cadaver.

20. The method of claim 19 further comprising desiccating said formulated nematode-infected insect cadaver.

21. The method of claim 19 wherein said starch is a cold-swelling starch.

22. A method for formulating nematode-infected insect cadavers comprising:
   (a) admixing an effective amount of a protein with water to form a first coating agent wherein said agent provides an adhesive surface on said cadaver;
   (b) applying said first coating agent to a nematode-infected insect cadaver to form an adhesive surface on said cadaver; and
   (c) coating said cadaver in a second coating agent selected from the group consisting of silica, kaolin, silicate, clay, bran, diatomaceous earth, zeolite, absorbent starch, lignin, and mixtures thereof; to form a formulated nematode-infected insect cadaver.

23. The method of claim 22 further comprising desiccating said formulated nematode-infected insect cadaver.

24. The method of claim 22 wherein said protein is selected from the group consisting of glutens, zeins, casein, whey, fish myofibbular protein and mixtures thereof.

25. The method of claim 22 wherein said gluten is selected from the group consisting of wheat gluten, corn gluten, soy gluten, rice gluten, oat gluten and mixtures thereof.

26. The method of claim 22 wherein said zein is selected from the group consisting of corn zein, wheat zein, soy zein, rice zein, oat zein and mixtures thereof.

27. A biocontrol composition comprising formulated biological organism-infected arthropod cadavers having a first coating agent that forms a surface which at least reduces sticking and/or rupture of said cadavers.

28. The biocontrol composition of claim 27 wherein said first coating agent contains a starch, carbohydrate, synthetic polymer, adhesive, oil, lipid, protein, or mixtures thereof.

29. The biocontrol composition of claim 27 wherein said cadaver containing first coating agent further comprises a second coating agent powder or granule selected from the group consisting of silica, kaolin, silicate, clay, bran, diatomaceous earth, zeolite, absorbent starch, lignin, and mixtures thereof.

30. The biocontrol composition of claim 27 wherein said formulated biological organism-infected arthropod cadaver is desiccated.

31. A biocontrol composition comprising biological organism-infected arthropod cadavers produced by a process comprising:
   (a) admixing an effective amount of a coating compound in a liquid to form a first coating agent wherein said coating agent provides a surface on a biological organism-infected arthropod cadaver which at least reduces sticking and rupture of said cadavers; and (b) applying to biological organism-infected arthropod cadavers said first coating agent to form a surface on said cadaver to at least reduce sticking and/or rupture of said cadavers.

32. The biocontrol composition of claim 31 wherein said first coating agent includes an antifungal agent.

33. The biocontrol composition of claim 31 wherein said formulated biological organism-infected arthropod cadaver is desiccated.

34. The biocontrol composition of claim 31 wherein said coating compound is selected from the group consisting of starch, carbohydrate, synthetic polymer, adhesive, oil, lipid, protein, and mixtures thereof.

35. The biocontrol composition of claim 31 wherein the process further comprises coating said cadaver with a first coating agent in a second coating agent powder or granule to form a formulated biological organism-infected arthropod cadaver.

36. The biological control composition of claim 35 wherein said second coating agent is selected from the group consisting of silica, kaolin, silicate, clay, bran, diatomaceous earth, zeolite, absorbent starch, lignin, and mixtures thereof.

37. A biocontrol composition comprising nematode-infected insect cadavers produced by a process comprising
   (a) admixing an effective amount of a coating compound with a liquid to form a first coating agent wherein said agent provides an adhesive surface on said cadaver and said coating compound is selected from the group consisting of starch, carbohydrate, synthetic polymer, adhesive, oil, lipid, protein, and mixtures thereof;
   (b) immersing a nematode-infected insect cadaver in said first coating agent to form an adhesive surface on said cadaver; and
   (c) coating said cadaver in a second coating agent selected from the group consisting of hydrated silica, fumed silica, kaolin, silicate, clay, bran, diatomaceous earth, zeolite, absorbent starch, lignin, and mixtures thereof; to form a formulated nematode-infected insect cadaver.

38. A biocontrol composition comprising nematode-infected insect cadavers produced by a process comprising:
   (a) admixing an effective amount of a protein with water to form a first coating agent wherein said agent provides an adhesive surface on said cadaver,
   (b) immersing a nematode-infected insect cadaver in said first coating agent to form an adhesive surface on said cadaver, and
   (c) coating said cadaver in a second coating agent selected from the group consisting of hydrated silica, fumed silica, kaolin, silicate, clay, bran, diatomaceous earth, zeolite, absorbent starch, lignin, and mixtures thereof; to form a formulated nematode-infected insect cadaver.

39. The biocontrol composition of claim 38 wherein said protein is a gluten or a zein.

40. The biocontrol composition of claim 38 wherein said gluten is selected from the group consisting of wheat gluten, corn gluten, soy gluten, rice gluten, oat gluten, and mixtures thereof.

41. The biocontrol composition of claim 38 wherein said formulated nematode-infected insect cadaver is desiccated.

* * * * *